(12) United States Patent
Hernández et al.

(10) Patent No.: US 8,703,893 B2
(45) Date of Patent: Apr. 22, 2014

(54) FOUR BRANCHED DENDRIMER-PEG FOR CONJUGATION TO PROTEINS AND PEPTIDES

(75) Inventors: José Ángel Ramón Hernández, Camagüey (CU); Fidel Raúl Castro Odio, Ciudad de la Habana (CU); Vivian-María Sáez Martinez, Ciudad de la Habana (CU); Rolando Páez Meircles, Ciudad de la Habana (CU); Eduardo Fernández Sánchez, Ciudad de la Habana (CU)

(73) Assignee: Centro de Ingenienia Genetica y Biotecnologia, Ciudad de la Habana (CU)

( * ) Notice: Subject to any disclaimer, the term of this patent is extended or adjusted under 35 U.S.C. 154(b) by 623 days.

(21) Appl. No.: 12/095,335

(22) PCT Filed: Nov. 20, 2006

(86) PCT No.: PCT/CU2006/000014
§ 371 (c)(1),
(2), (4) Date: Oct. 6, 2008

(87) PCT Pub. No.: WO2007/062610
PCT Pub. Date: Jun. 7, 2007

(65) Prior Publication Data
US 2009/0082537 A1  Mar. 26, 2009

(30) Foreign Application Priority Data
Nov. 30, 2005 (CU) .................. 2005-0241

(51) Int. Cl.
*A61K 31/765* (2006.01)
*C12N 9/70* (2006.01)

(52) U.S. Cl.
USPC ........ 527/200; 424/78.38; 524/54.1; 528/420

(58) Field of Classification Search
USPC ........... 527/200; 528/420, 407, 406; 435/188, 435/177; 424/94.3; 530/402; 546/300
See application file for complete search history.

(56) References Cited

U.S. PATENT DOCUMENTS

| | | | |
|---|---|---|---|
| 5,932,462 A * | 8/1999 | Harris et al. | 435/188 |
| 7,026,440 B2 * | 4/2006 | Bentley et al. | 528/407 |
| 2005/0033058 A1 * | 2/2005 | Huang et al. | 546/300 |

FOREIGN PATENT DOCUMENTS

| | | | |
|---|---|---|---|
| EP | 1333036 A1 | | 8/2003 |
| EP | 1479711 A1 | | 11/2004 |
| WO | 9621469 | | 7/1996 |
| WO | 03040211 A2 | | 5/2003 |
| WO | 03059987 A1 | | 7/2003 |
| WO | 03093346 A1 | | 11/2003 |
| WO | 2005000360 A2 | | 1/2005 |
| WO | 2005014049 A2 | | 2/2005 |
| WO | 2006019950 A2 | | 2/2006 |
| WO | 2006087354 A2 | | 8/2006 |
| WO | 2006089228 A2 | | 8/2006 |

OTHER PUBLICATIONS

Lata et al, "Stable and Functional Immobilization of Histidine-Tagged Proteins via Multivalent Chelator Headgroups on a Molecular Poly(ethylene glycol) Brush," Anal. Chem. 2005, 77:1096-1105.

* cited by examiner

*Primary Examiner* — James J Seidleck
*Assistant Examiner* — S. Camilla Pourbohloul
(74) *Attorney, Agent, or Firm* — Hoffmann & Baron LLP

(57) ABSTRACT

A polymeric dendrimer-like structure with four branches of monomethoxy-polyethylene glycol that can be represented as:

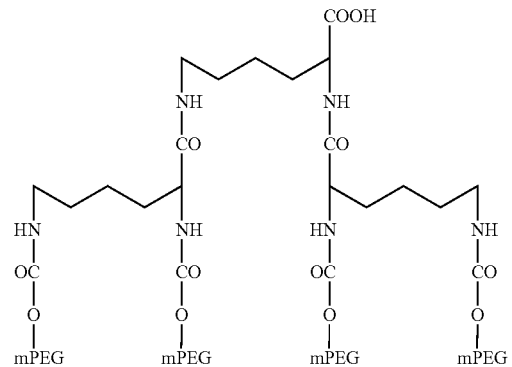

The carboxylic group of the previous structure can be functionalized for the production of conjugates of pharmaceutical interest. The binding of this dendrimer-like polyethylene glycol to therapeutic proteins improves their in vitro and in vivo stability.

2 Claims, 1 Drawing Sheet

FOUR BRANCHED DENDRIMER-PEG FOR CONJUGATION TO PROTEINS AND PEPTIDES

This application is the U.S. National Phase of, and Applicants claim priority from, International Application Number PCT/CU2006/000014 filed 20 Nov. 2006 and Cuban Application bearing Serial No. CU-2005-0241 filed 30 Nov. 2005, which are incorporated herein by reference.

TECHNICAL FIELD

The present invention is related to a dendrimer-like polymeric structure with four branches of polyethylene glycol (PEG), for obtaining conjugates of pharmaceutical interest.

PREVIOUS ART

The benefits of the conjugation of therapeutic proteins with polyethylene glycol on several pharmacological properties are well known. For example, the half-life in blood increases due to different causes, between them: the polymeric residue can prevent the attack of proteases and the recognition of the drug by the immune system and the significantly higher hydrodynamic volume of the conjugate with respect to the native protein diminishes significantly the kidney filtration. Even though in many cases the PEGylation affects the biological activity of a protein in vitro, the substantial increase of the lifetime in blood makes more effective its therapeutic action (Harris J. M. y Chess R. B. (2003) Effect of pegylation on pharmaceuticals. *Nat. Rev. Drug Discov.* 2:214-21).

The PEGylation also blocks sterically the ways of degradation induced by hydrophobic interactions and generates sterical non-specific obstacles that diminish the intermolecular interactions involved in the thermal instability of the proteins. All this makes that the PEGylated proteins have a higher physical stability than the unmodified molecules, a very useful property for the development of a final pharmaceutical preparation (Harris J. M. y Chess R. B. (2003) Effect of pegylation on pharmaceuticals. *Nat. Rev. Drug Discov.* 2:214-21).

The reagent commonly used for the conjugation of proteins is the polyethylene glycol methylated in one of its extremes, known as monomethoxypolyethylene glycol (mPEG). The fact that a methyl group protects one of the ends of the PEG chain allows its activation only by the other extreme, a monofunctional reagent. This is very important for the conjugation of therapeutic proteins since their conjugation to bifunctional or polyfunctional reagents in general leads to a crosslinking that affects the biological activity of the protein. The mPEG molecules have always a small fraction of non-methylated polymer, the diol fraction. The diol fraction is bigger in the mPEG of higher molecular mass due to the fact that it is more difficult to control the polymerization process for very long chains (Roberts M. J., Bentley M. D., Harris J. M. (2002) Chemistry for peptide and protein PEGylation. *Adv. Drug Deliv. Reviews* 54:459-76).

One of the first molecules derived from PEG was the one synthesized by reaction with cyanogen chloride. But the conjugation experiments with this reagent provoked an extensive PEGylation. This is undesirable for therapeutic proteins, since a high PEGylation degree causes a sudden decline in biological activity, due to the direct blocking of the active sites, or by topological changes that hide these sites from the accessible protein surface. Usually the desired conjugate is the one where there is only one PEG residue per each protein molecule; this molecule is known as monoPEGylated.

Since the 1980's "softer" active groups begin to be used. These are mainly N-hydroxysuccinimide esters though other groups were also used. Three of the most common groups are: the succinimidyl succinate, tresylate and succinimidyl carbonate. This generation of activated PEGs is known as First Generation (Roberts M. J., Bentley M. D., Harris J. M. (2002) Chemistry for peptide and protein PEGylation. *Adv. Drug Deliv. Reviews* 54:459-76).

In the second half of the 1990s arises the Second Generation of activated PEGs. There were two important advances here: groups that allowed a more selective PEGylation (for example: aldehyde group that conjugates preferably by the N-terminal of the proteins) and branched structures (Roberts M. J., Bentley M. D., Harris J. M. (2002) Chemistry for peptide and protein PEGylation. *Adv. Drug Deliv. Reviews* 54:459-76). Examples of the branched PEGs are monofunctional with two branches (U.S. Pat. No. 5,932,462), the tetrafunctional with four branches and the octafunctional with eight branches. The more useful activated PEGs for the conjugation of therapeutic proteins are the monofunctional ones, since they avoid the crosslinking between the protein and the polymer. The branched PEGs have also an umbrella like structure that allows a better protection of the protein surface.

The monofunctional PEG of two branches has allowed obtaining a conjugate with interferon alpha 2a that has shown to have better results in clinic than the native protein (Rajender Reddy K., Modi M. W., Pedder S. (2002) Use of peginterferon alfa-2a (40 KD) (Pegasys) for the treatment of hepatitis C. *Adv. Drug Deliv. Reviews* 54:571-86).

With the present technology for mPEG synthesis, only 30 kDa chains can be obtained, reason why reagents with two branches allow obtaining molecular masses with a maximum of 60 kDa. It is desirable to have structures with monofunctional PEG of higher molecular mass that allow explore a wider range of conjugates to obtain the optimum value in certain proteins. However, in none of the previously described reports has been used, characterized or mentioned a reagent for PEGylation that would be monofunctional and with more than two PEG chains. In case of obtaining a reagent with more than two PEG chains, conjugates of higher molecular mass could be obtained and, in addition to the previously mentioned advantage, this could allow using shorter mPEG linear branches to generate PEGylation reagents of similar molecular mass to the two branched-structures. These lower size branches would have a smaller diol fraction, making easier the synthesis processes.

EXPLANATION OF THE INVENTION

The present invention solves the above mentioned problem, providing a monofunctional dendrimer-like structure that has four mPEG branches. This structure allows obtaining conjugates with polymeric residues of until 120 kDa. This fact allows exploring conjugates with a great variety of molecular masses, including those of high molecular mass. Moreover, using this approach PEG molecules with a molecular mass similar to that of other branched monofunctional reagents can be obtained, but with linear chains of lower molecular mass.

In a preferred embodiment of the present invention a polymeric structure is obtained, where the molecular mass of the PEG chain is between 5,000 and 30,000 Da, and the total molecular mass is between 20,000 and 120,000 Da.

The use of small linear chains almost allowed eliminating the diol contamination typical of bigger linear PEG molecules. Unexpectedly, conjugates with our structure had a much higher physico-chemical stability (resistance to high temperatures and degradation by proteases) than that of conjugates with similar molecular mass, but prepared with the structures of only two branches. Also unexpectedly, they had a higher mean life time in blood. Another unexpected result was that the conjugates with our dendrimer-like structure were more homogenous, with lower position isomers than those obtained with conjugates with a similar molecular mass but with only two branches.

The dendrimer-like four-branched monofunctional PEG is obtained in two main steps. The first step is the synthesis of two branched-derivatives by the union of two linear PEG molecules to a core that can be, for example, a lysine. A similar process has been used by other authors with good results (U.S. Pat. No. 5,932,462). The second step is the union of two molecules of two branched-derivates to a core similar to the previous one to obtain the four branched-derivate. In order to join the two linear PEG branches to a core in the first step, they need to have an active group. This group can be chosen from some of the known in the state of the art. For example, succinimidyl succinate, succinimidyl carbonate, p-nitrophenylcarbonate, succinimidyl propionate, succinimidyl butanoate between others. A preferred linear activated PEG in the present invention is the succinimidyl carbonate. This is due to main different reasons: the good reaction yield between this reagent and the cores with free amino groups, and the ease of the production process of this functionalized PEG. This synthesis process (Miron T., Wilchek M. (1993) A Simplified Method for the Preparation of Succinimidyl Carbonate Polyethylene Glycol for Coupling to Proteins. *Bioconjugate Chem.* 4:568-69) is known by those working in the field:

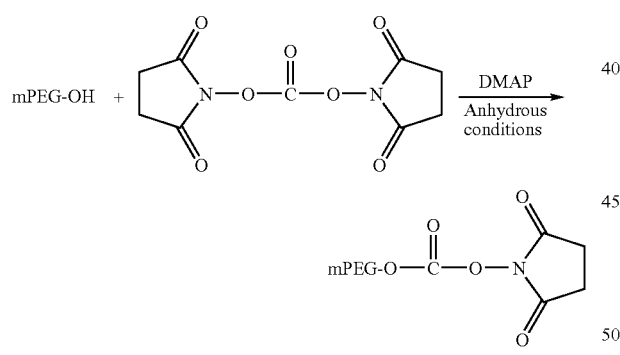

Once the linear activated PEG is ready, the first step is easily completed by its reaction with the molecule selected as core. In a preferred embodiment of this invention the core is L-lysine due to its biocompatible nature, with two free amino groups and a carboxylic group that can be used to be activated later.

The two branched-derivate is easily purified from the reaction mixture by chromatographic methods. This two branched-derivate is activated for the subsequent reaction with a core molecule and the synthesis of the four branched-derivate. This product can be activated in different ways, but a preferred one due to its efficacy and facility is the formation of an N-hydroxysuccinimide ester.

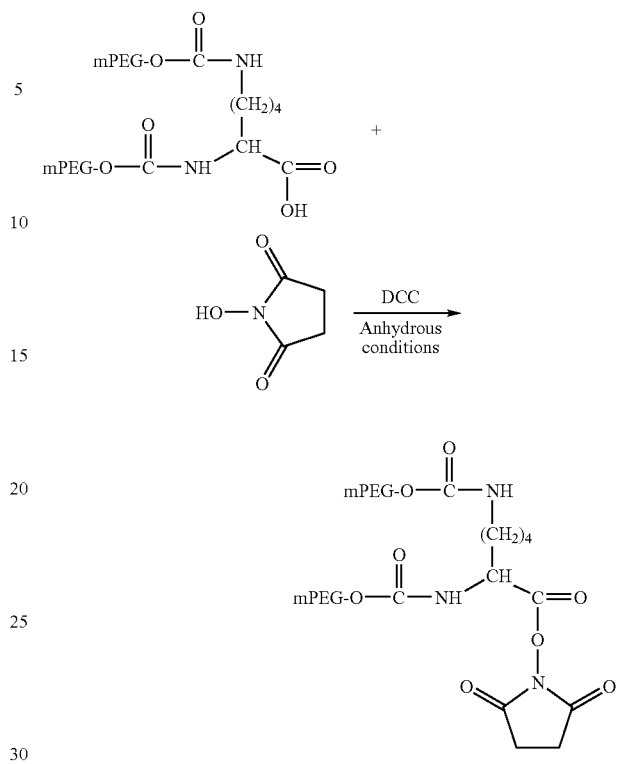

This procedure has been used successfully for the activation of carboxylic groups with structures that contain PEG chains, as N-hydroxysuccinimide ester (U.S. Pat. No. 4,732,863 y U.S. Pat. No. 5,932,462).

The second stage of the preparation of the four branched-derivate consists in the reaction of the two branched-derivate with a core molecule, where, as well as in the first stage of this invention; a preferred embodiment of this invention is the L-lysine as a core.

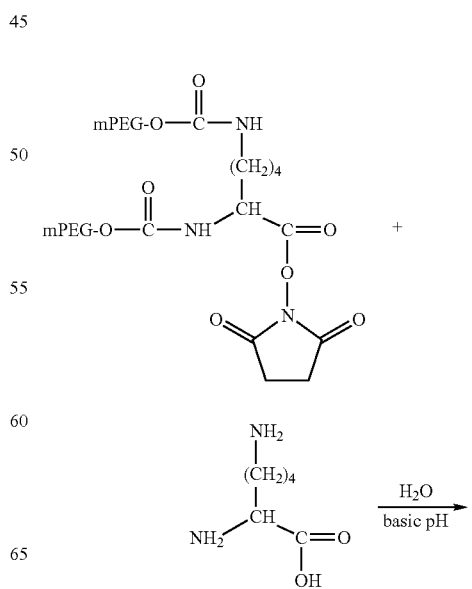

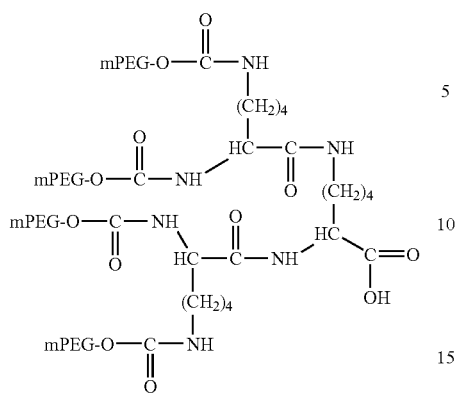

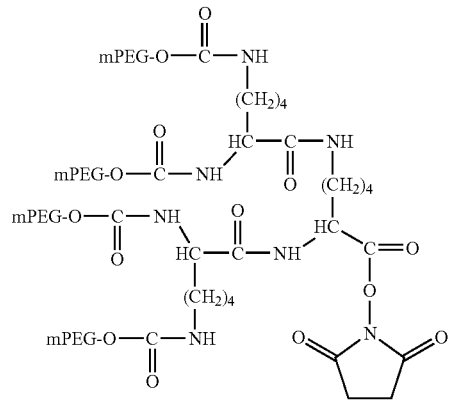

The derivate of interest is easily purified from the reaction mixture by chromatographic methods.

This dendrimer-like PEG molecule can be activated using different reactive groups for its conjugation to proteins. Any of the functional groups used for the activation of other PEG structures can be used for the dendrimer-like PEG described in this patent. Some examples of these groups are: N-hydroxysuccinimide esters, succinimidyl carbonate, different types of aldehydes, maleimides, etc. Other types of groups that allow the union of this structure to proteins are the chelating groups nitriloacetate (NTA), which can conjugate the histidines residues present in a peptide skeleton through a transition metal. The selection of the reactive group will depend on the protein residue to which we want to join the PEG molecule.

For example, if there is preference for union with free amino groups, the dendrimer-like polymer can be activated as N-hydroxysuccinimide ester. The N-hydroxysuccinimide ester is therefore obtained as a materialization of this invention, following the same procedure described for the activation of the two branched-structure of the stage 1.

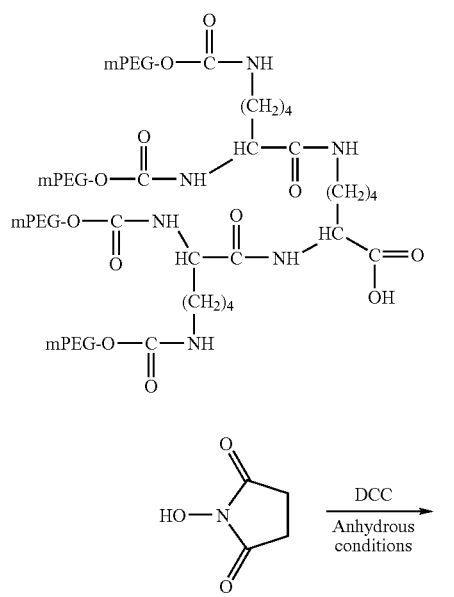

The conjugation of the protein with activated PEG takes place in an appropriate buffered solution. The characteristics of the buffered solution depend, among other factors, on the functional group of the polymer and the objective of the conjugation. For example, if it is desirable to conjugate by the free amino groups with a functionalized PEG as N-hydroxysuccinimide ester, the conjugation sites can be predicted, until certain degree, using a predetermined pH. A pH value of about 9 will favor the conjugation through the ε-amino group of the lysins.

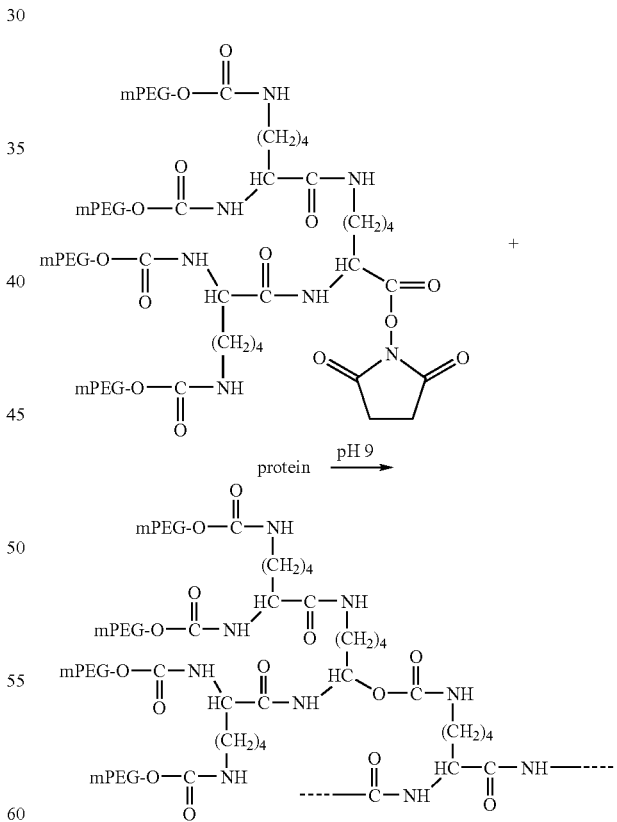

Another example is that in conjugation with aldehyde function, a slightly acid pH will allow that the PEGylation occur preferably on the N-terminal extreme of the protein. The subsequent purification of the conjugate of interest can be performed by different chromatographic techniques.

In a materialization of the invention, conjugates are described where the nucleophilic group is comprised in a biomolecule selected from the group consisting in proteins, peptides and polypeptides.

Some chemical, physical and biological properties of the conjugates must be analyzed to achieve a characterization as complete as possible of the purified conjugate. For example, the concentration of the conjugate can be usually determined by ultraviolet spectroscopy (absorbance at 280 nm), since the PEG residue almost does not affect the extinction coefficient of the protein. The purity of the purified product must be determined preferably by sodium dodecyl sulfate polyacrylamide gel electrophoresis (SDS-PAGE), since the chromatographic methods like gel filtration can resolve poorly the signals corresponding to the conjugate of interest and the contaminants. Other physico-chemical properties can be studied by the usual procedures.

As a result of this work, a preferred realization of this invention describes the preparation of conjugates where the protein is selected from the group consisting of: interferon alpha-2b, streptokinase, granulocyte colony stimulating factor, erythropoietin or epidermal growth factor.

DETAILED EXPOSITION OF THE MODES OF PREPARATION/EXAMPLES

Example 1

Figure 1:
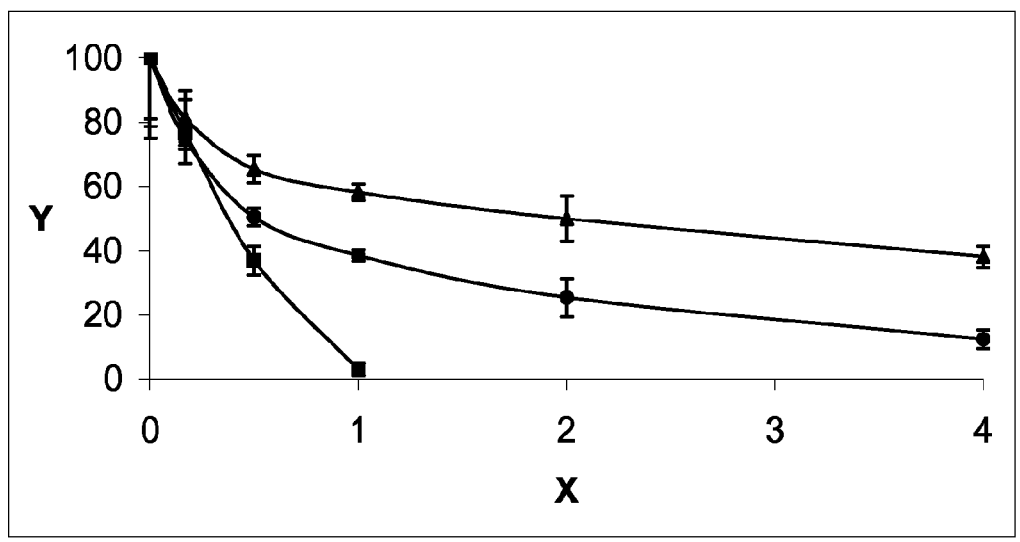
FIG. 1. Protection against degradation by proteases. The X-axis represents time in hours and Y-axis the amount of non-degraded protein expressed in percent of the amount at time zero.

Synthesis of PEG Activated as N-Hydroxysuccinimide Ester Obtaining of the Structure and Activation Obtaining the Succinimidylcarbonate of Monomethoxypolyethylene Glycol (SC-PEG)

Fifteen grams of monomethoxypolyethylene glycol with molecular mass of 12,000 Da ($mPEG_{12K}$) were dissolved in 500 mL of toluene and dried azeotropically for 3 hours. After this time the volume was reduced to 250 mL and the mixture was cooled down to room temperature. The following reagents were added to this solution: 60 mL of dry dichloromethane, 2 g of disuccinimidyl carbonate (DSC) dissolved in 15 mL of dry acetone, and 1 g of dimethylaminopiridine dissolved in 10 mL of a 3:1 mix of toluene:DCM. The reaction took place overnight (16 h) with stirring. The reaction mixture was precipitated with 1 L of cold diethyl ether and the precipitate was collected by filtration. This product was recrystallized three times dissolving in acetone and precipitating with diethyl ether. The final product was dried under high vacuum and stored under nitrogen at −20° C. The final yield of the process was higher than 90%. The fraction of activated PEG was determined by reaction with glycil-glycine and quantification of free amino groups by reaction with TNBS.

Obtaining of biPEGylated Lysine (Lys-2PEG)

Twelve grams of $SC-PEG_{12K}$ reacted with 46 mg of L-(+)-lysine dissolved at a 0.2 mg/mL concentration in 100 mM borate buffer, pH 8.5. The reaction took place at room temperature with stirring for 16 hours. After this time, the reaction mixture was diluted 5 times in bi-distilled water and the pH was adjusted with hydrochloric acid. The PEG was extracted three times with one volume of DCM. The pool of the three extraction fractions was dried with anhydrous sodium sulfate and filtered. The PEG solution in DCM was concentrated until 20 mL in a rotary evaporator. The concentrate was precipitated with 120 mL of cold diethyl ether, collected by filtration and dried at high vacuum. The Lys-2PEG was separated from the rest of the components of the reaction mixture by ion exchange chromatography with DEAE Sepharose.

A column that contained 1 liter of the chromatographic matrix was equilibrated with 3 volumes of the 100 mM borate buffer solution at pH 7.5 and then washed with 5 volumes of bi-distilled water. Ten grams of the reaction mixture were applied dissolved in bi-distilled water at 5 mg/mL. The PEG that did not react was eliminated washing the column with two volumes of bi-distilled water and the Lys-2PEG was eluted with a 1 mM solution of sodium chloride. The pH of this fraction was adjusted to 3 with hydrochloric acid and was extracted three times with one volume of DCM. The pool of the three extraction fractions was dried with anhydrous sodium sulfate and then filtered. The PEG solution in DCM was concentrated until 10 mL in a rotary evaporator. The concentrate was precipitated with 60 mL of cold diethyl ether, separated by filtration and dried under high vacuum. The purity degree was determined by SDS-PAGE, staining the gel with a barium chloride solution at 5% and 100 mM iodine. The molecular mass determined by MALDI-TOF was 23.0-24.5 kDa. The total yield of the process was higher than 40%.

Activation of the biPEGylated Lysine as N-Hydroxysuccinimide Ester ($PEG_{2,12K}$-NHS).

Six grams of Lys-2PEG were dissolved in 20 mL of dry DCM, and 60 mg of N-hydroxysuccinimide and 250 mg of N,N'-dicyclohexylcarbodiimide (DCC) were added. The reaction was kept under stirring for 24 hours at room temperature. The mix was filtered and concentrated by rotary evaporation until 5 mL. The product was precipitated with 20 mL of cold diethyl ether, and crystallized three times dissolving in acetone and precipitating with diethyl ether. The final product was dried under high vacuum and stored under nitrogen at −20° C. The total yield of the process was higher than 95%. The fraction of activated PEG was determined by reaction with glycil-glycine and the number of free amino groups was quantified by reaction with TNBS.

Obtaining of the Dendrimer-Like Four-Branched PEG

Five grams of $PEG_{2,12K}$-NHS were put in reaction with 7 mg of L-(+)-lysine dissolved in 0.1 mg/mL of 100 mM borate buffer solution, pH 8.5. The reaction took place at room temperature with stirring for 16 hours. After this time, the reaction mixture was diluted 5 times with bi-distilled water and the pH was adjusted to 3 with hydrochloric acid. The PEG was extracted three times with one volume of DCM. The pool of the three extraction fractions was dried with anhydrous sodium sulfate and filtered. The PEG solution in DCM was concentrated until 5 mL in a rotary evaporator. The concentrate was precipitated with 30 mL of cold diethyl ether, separated by filtration and dried under high vacuum. The dendrimer-like four branched-PEG was purified by size exclusion chromatography in a G3000PW column. The pH of the fraction containing the desired structure was adjusted to 3 with hydrochloric acid, and extracted three times with one DCM volume. The pool of the three extraction fractions was dried with anhydrous sodium sulfate and filtered. The PEG solution in DCM was concentrated until 5 mL in a rotary evaporator. The concentrate was precipitated with 30 mL of cold diethyl ether, separated by filtration and dried under high vacuum. The purity degree was determined by SDS-PAGE staining the gel with a barium chloride solution at 5% and 100 mM iodine, and was higher than 98%. The molecular mass, determined by MALDI-TOF was of 45.5-50 kDa. The total yield of the process was higher than 30%.

Functionalization of the Dendrimer-Like Four Branched-PEG as an N-Hydroxysuccinimide Ester ($PEG_{4,12K}$-NHS)

One and half gram of dendrimer-like four branches PEG were dissolved in 5 mL of dry DCM and 9 mg of N-hydroxysuccinimide and 37 mg of N,N'-dicyclohexylcarbodiimide were added. The reaction was kept under stirring for 24 hours at room temperature. The product was filtered and then precipitated with 20 mL of cold diethyl ether. The precipitate was re-crystallized three times dissolving in acetone and precipitating with diethyl ether. The final product was dried under high vacuum and was kept under nitrogen at −20° C. The total yield of the process was higher than 95%. The fraction of activated PEG was determined by reaction with glycil-glycine and the amount of free amino groups was determined by reaction with TNBS.

Example 2

Obtaining of IFN-α2b Conjugated with $PEG_{4,12K}$-NHS

Conjugation Reaction

Four grams of dendrimer-like four branched-PEG activated as N-hydroxysuccinimide ester ($PEG_{4,12K}$-NHS) were added to a solution that contained 1 gram of IFN-α2b at 6 mg/mL in a 120 mM borate buffer solution, pH 8.5. The reaction was kept for 1 hour at 4° C. under gentle stirring, and then stopped diluting 50 times with 10 mM sodium acetate buffer solution, pH 4. The yield of the reaction was determined by densitometry analysis of an SDS-PAGE staining with Coomassie Brilliant Blue R-250. The fraction of monoPEGylated IFN-α2b with the dendrimer-like four branched-PEG was higher than 40%.

Purification of MonoPEGylated IFN-α2b with Dendrimer-Like Four Branched-PEG

An XK 50/60 column (Pharmacia) that contained 500 mL of Fractogel EMD 650 (M) COO— was equilibrated with 3 volumes of 10 mM acetate buffer solution, pH 4, at a flow of 40 mL/min. The solution containing the reaction mixture was applied on the column at the same flow. The PEG that did not react and the conjugates with more than one PEG residue were eliminated with a 2-hour wash with 40 mM acetate buffer solution, pH 4, with 25 mM sodium chloride. The monoPEGylated conjugate was eluted with 50 mM sodium acetate buffer solution, pH 4, with 150 mM sodium chloride. The purity was higher than 96% and the main contaminants were unmodified interferon and the biPEGylated conjugate. The fraction of interest was concentrated until 200 mL and applied on an XK 50/60 column (Pharmacia) that contained 1 L of Sephadex G-25 equilibrated with 50 mM phosphate buffer solution, pH 7, with 100 mM of sodium chloride. The monoPEGylated interferon with dendrimer-like four branched-PEG was filtered through a cellulose acetate membrane with 0.2 μm pore size and stored at 4° C.

Example 3

Physico-Chemical Characterization of the $PEG_{4,12K}$-IFN-α2b

Determination of the Conjugate Concentration

The concentration of the conjugate as a function of the protein residue was determined by UV-absorbance at 280 nm. One absorbance unit was considered to be equivalent to a concentration of 1 mg/mL.

Determination of the Molecular Mass of the Conjugate

The molecular mass of the conjugate was determined by MALDI-TOF. The average molecular mass expected for the dendrimer-like four branched-PEG was 48,000 Da and that of IFN-α2b was 19,200 Da, therefore the theoretical mass of the conjugate was 67,200 Da. The calculated mass for the $PEG_{4,12K}$-IFN-α2b was of 64,000-70,000 Da.

Example 4

Biological Characterization of the $PEG_{4,12K}$-IFN-α2b Conjugate

Immunological Identification of the Conjugate in an ELISA-Type Assay

Samples of the conjugate at different concentrations as well as negative control were applied on an ELISA microtiter plate recovered with a monoclonal antibody against IFN-α2b. Next, another monoclonal antibody that recognizes another epitope of IFN-α2b, conjugated to horseradish peroxidase was added. It was considered that samples were immunologically recognized when the absorbance of the conjugate samples was higher than the average of the absorbance of negative samples plus three times the standard deviation of these values. The samples were recognized in all the cases.

In Vitro Antiviral Activity

The in vitro antiviral activity was determined by the inhibition of the cytopathic effect produced by the Mengovirus on Hep-2 cells (ATCC No. CCL23). Serial dilutions (1:2) of the conjugate in minimal essential media with 2% fetal bovine serum and 40 μg/mL of gentamycin were mixed in cell monolayers in 96-well microtiter plates. The plates were incubated at 37° C. for 24 hours under a 3% carbon dioxide atmosphere and 95% relative humidity. The virus ($10^7$ TCID) was added and the plates were incubated until the cytopathic effect (90% of cell lysis) was evident. The level of cell destruction was measured by staining of the cells with crystal violet. The activity of each sample was expressed in international units (IU), evaluating with the IFN-α2b international standard 69/19 from the World Health Organization, and the obtained results are presented in table 1.

TABLE 1

In vitro antiviral activity of native IFN-α2b and conjugated to dendrimer-like four branched-PEG.

| Sample | Preparation | Antiviral activity (IU/mg) |
| --- | --- | --- |
| Native Interferon | — | $2.0 \times 10^8$ |
| Interferon modified with | 1 | $1.1 \times 10^7$ |
| dendrimer-like four | 2 | $0.9 \times 10^7$ |
| branched-PEG | 3 | $1.2 \times 10^7$ |

In Vitro Antiproliferative Activity.

The in vitro antiproliferative activity was measured by the capacity of the conjugated IFN-α2b of inhibiting the growth of Daudi cells (Burkitt Lymphoma). The results showed that the in vitro activity of PEG$_{4,12K}$-IFN-α2b was equivalent to a 5% of that of the unmodified IFN-α2b.

Example 5

Physico-Chemical Stability of the PEG$_{4,12K}$-IFN-α2b

Resistance to Degradation by Proteases

Forty microliters of a 4% sodium bicarbonate solution, pH 8, containing 400 µg/mL of native IFN-α2b, conjugated to two or four branched-PEG with similar molecular masses were mixed with 10 µL of a 160 µg/mL trypsin solution. The sample was incubated at 37° C. for certain time. The reaction was stopped with 10 µL of trifluoroacetic acid. The residual amount of protein (conjugated or not) was estimated by the disappearance of the band in a SDS-PAGE analysis, stained with Coomassie Brilliant Blue. The results (FIG. 1) show that the protection that brings the four-branched PEG structure (▲) to degradation of the IFN-α2b conjugate is superior to that produced by the two branched-structure of similar molecular mass (●).

Thermal Stability

Figure 2:
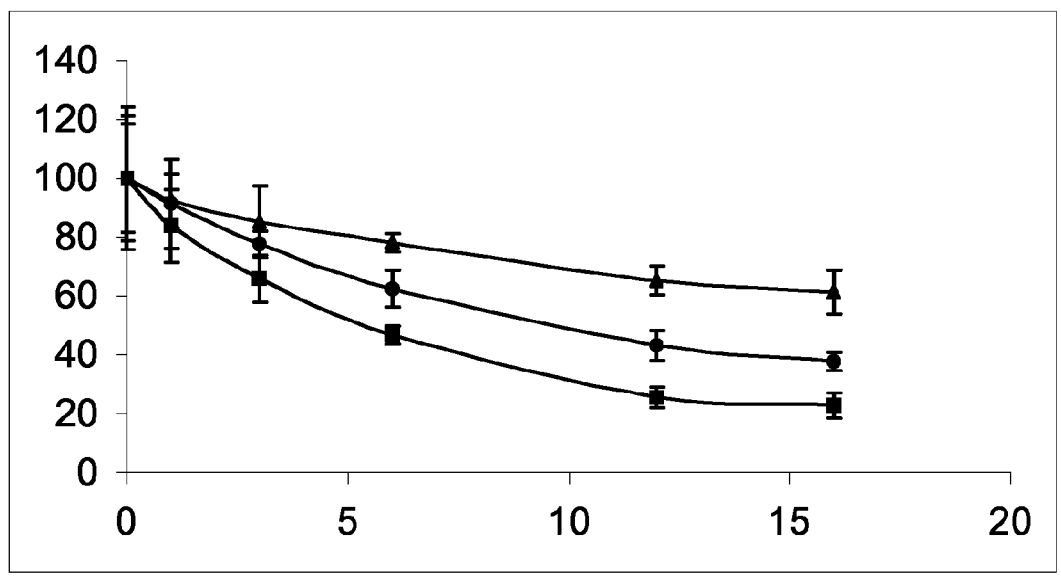
FIG. 2. Thermal resistance. The X-axis represents the time in days and Y-axis the amount of non-degraded protein expressed in percent of the amount at time zero.

To determine the effect on stability of the IFN-α2b conjugation with dendrimer-like four branched-PEG, samples of the native and conjugated protein were incubated at 60° C. in a phosphate buffered saline solution. A sample of IFN-α2b conjugated to two-branched-PEG with similar molecular mass was used as control. Samples were withdrawn at certain times and the residual amount of the protein (conjugated or not) was estimated by the disappearance of the band in a SDS-PAGE analysis stained with Coomassie Brilliant Blue. The results (FIG. 2) show that the thermal stability of the conjugate with four-branched structure (▲) is higher than that of the other two cases [native IFN (■), IFN conjugated to two branched structure (●)].

Example 6

Pharmacokinetics of PEG$_{4,12K}$-IFN-α2b

The comparative pharmacokinetic study between the unmodified interferon and the protein conjugated to dendrimer-like four branched-PEG was performed in New Zealand rabbits with an average weight of 2 kg. IFN-α2b conjugated to two-branched-PEG was used as control. The biomolecules were injected by subcutaneous route at 150 µg of protein per kg of weight. Blood samples were taken for an interval of 144 hours at prefixed times. The samples were centrifuged and the serum was separated and stored at −20° C. until analysis. The IFN-α2b concentration (conjugated or not) was determined by an ELISA-type assay with monoclonal antibodies specific for this cytokine. The interpretation was based on a classical compartment mammillary model. The results are presented in Table 2.

TABLE 2

Compared pharmacokinetics of native IFN-α2b and conjugated to two branched-PEG and to PEG$_{4,12K}$-IFN-α2b.

| Parameter | Native IFN-α2b | Two branched IFN-PEG | PEG$_{4,12K}$-IFN-α2b |
|---|---|---|---|
| AUC, µg · h/mL | 339.12 | 74907.38 | 88952.15 |
| t$_{1/2}$, h | 2.38 | 50.48 | 63.58 |
| MRT, h | 4.33 | 90.68 | 105.23 |

Example 7

Conjugation of Other Therapeutic Proteins to Dendrimer-Like Four Branched-PEG

Other therapeutic proteins like recombinant streptokinase (r-SK), erythropoietin (EPO), granulocyte-colony stimulating factor (G-CSF) and epidermal growth factor (EGF), were conjugated with the dendrimer-like four branched-PEG. The effect of the conjugation on the degradation rate by proteases was evaluated.

Conjugation of Dendrimer-Like Four Branched-PEG Activated as Ester of N-Hydroxysuccinimide.

100 milligrams of dendrimer-like four branched-PEG activated as ester of N-hydroxysuccinimide (PEG$_{4,12K}$-NHS) were added to a solution containing 25 mg of the therapeutic protein at 6 mg/mL in a 120 mM borate buffer solution, pH 8.5. The reaction was kept for 1 hour at 4° C. with gentle stirring. The reaction was stopped by 50-fold dilution with 10 mM sodium acetate buffer, pH 4. The reaction yield was determined by densitometry analysis from the SDS-PAGE of samples stained with Coomassie Brilliant Blue R-250. The fraction of monoPEGylated protein with dendrimer-like four branched-PEG was higher than 30% in all the cases.

Conjugation with Dendrimer-Like PEG Activated as Aldehyde.

100 milligrams of dendrimer-like four branched-PEG activated as aldehyde (PEG$_{4,12K}$-ALD) were added to a solution containing 15 mg of the therapeutic protein at 4 mg/mL in 100 mM acetate buffer solution, pH 5, with 20 mM of sodium cyanoborohydride. The reaction lasted 24 hours at 4° C. with gentle stirring, and was stopped by 20-fold dilution with 1 mM HCl. The yield of the reaction was determined by densitometry analysis from the SDS-PAGE of samples stained with Coomassie Brilliant Blue R-250. The fraction of the monoPEGylated protein with the dendrimer-like four branched-PEG was higher than 30% in all the cases.

Effect of the Conjugation of Dendrimer-Like Four Branched-PEG on the Degradation of Proteins by Proteases Forty microliters of a 4% bicarbonate solution, pH 8, containing 400 µg/mL of the native protein or conjugated to four branched-PEG were mixed with 10 µL of a 160 µg/mL trypsin solution. The sample was incubated at 37° C. for 4 hours with gentle stirring. After this time the reaction was stopped with 10 µL of trifluoroacetic acid. The residual amount of protein (conjugated or not) was estimated by the disappearance of the band in a SDS-PAGE analysis stained with Coomassie Brilliant Blue. The results (Table 3) indicate that the conjugation to dendrimer-like four branched-PEG protects the conjugated proteins from degradation by trypsin. In all the cases more than 35% of the protein has not been digested after 4 hours of reaction with trypsin, independently of the employed chemical conjugation method. However, no sign could be detected after this reaction time for native proteins.

TABLE 3

Fraction (%) of undigested protein with respect to the amount of protein before the reaction

| Protein | Native | Conjugated with PEG$_{4,12K}$-NHS | Conjugated with PEG$_{4,12K}$-ALD |
|---|---|---|---|
| r-SK | 0% | 38.2 ± 1.5% | 41.5 ± 0.9% |
| EPO | 0% | 39.8 ± 2.3% | 37.5 ± 1.7% |
| G-CSF | 0% | 45.6 ± 3.4% | 42.1 ± 2.9% |
| EGF | 0% | 35.1 ± 4.4% | 37.6 ± 4.8% |

The invention claimed is:
1. A conjugate comprising a) a polymeric dendrimer-like structure including four branches of monomethoxy-polyethylene glycol that can be represented like

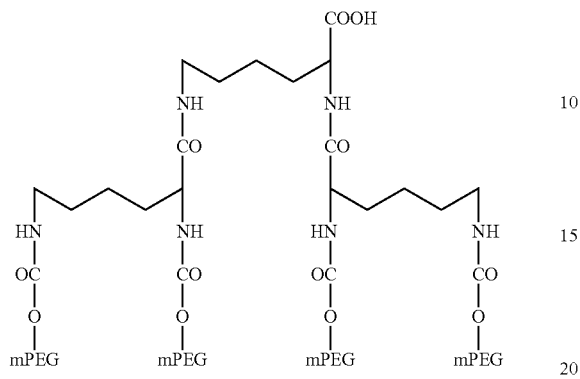

wherein the total molecular mass is between 45,500 and 50,000 Da, and b) a nucleophilic group which comprises interferon alpha 2-b.

2. A conjugate according to claim 1, wherein said polymeric structure is activated for conjugation with said nucleophilic group, obtained by functionalization of the carboxylic group.

* * * * *